United States Patent [19]

Shimoni et al.

[11] Patent Number: 4,617,938
[45] Date of Patent: Oct. 21, 1986

[54] METHOD AND SYSTEM FOR DISTINGUISHING R-WAVE ELECTROCARDIOGRAPH SIGNALS FOR SYNCHRONIZING PURPOSES

[76] Inventors: Yair Shimoni, c/o Elscint Ltd., P.O. B. 5258; Amir Gilad, 42 Sederot Hatzvi; Alex Shapira, c/o Elscint Ltd., P.O. B. 5258, all of Haifa, Israel

[21] Appl. No.: 686,389

[22] Filed: Dec. 26, 1984

[51] Int. Cl.⁴ .............................................. A61B 5/04
[52] U.S. Cl. .................................................. 128/708
[58] Field of Search ............... 128/695, 696, 702, 703, 128/704, 706, 708, 710, 902

[56] References Cited

U.S. PATENT DOCUMENTS

| | | | |
|---|---|---|---|
| 3,878,833 | 4/1975 | Arneson et al. | 128/708 |
| 4,173,221 | 11/1979 | McLaughlin et al. | 128/696 |
| 4,240,442 | 12/1980 | Andresen et al. | 128/708 |
| 4,250,889 | 2/1981 | Levin | 128/708 |
| 4,263,919 | 4/1981 | Levin | 128/708 |

*Primary Examiner*—William E. Kamm
*Attorney, Agent, or Firm*—Sandler & Greenblum

[57] ABSTRACT

An improved ECG system for on-line analysis of the signals received from exercise ECGs whereby the signals from at least a pair of electrodes are differentiated and compared to find maximum slopes of the same sign occuring at the same time, which characteristics are deemed indicative of "R" waves.

16 Claims, 12 Drawing Figures

TRACE TAKEN DURING EXERCISE

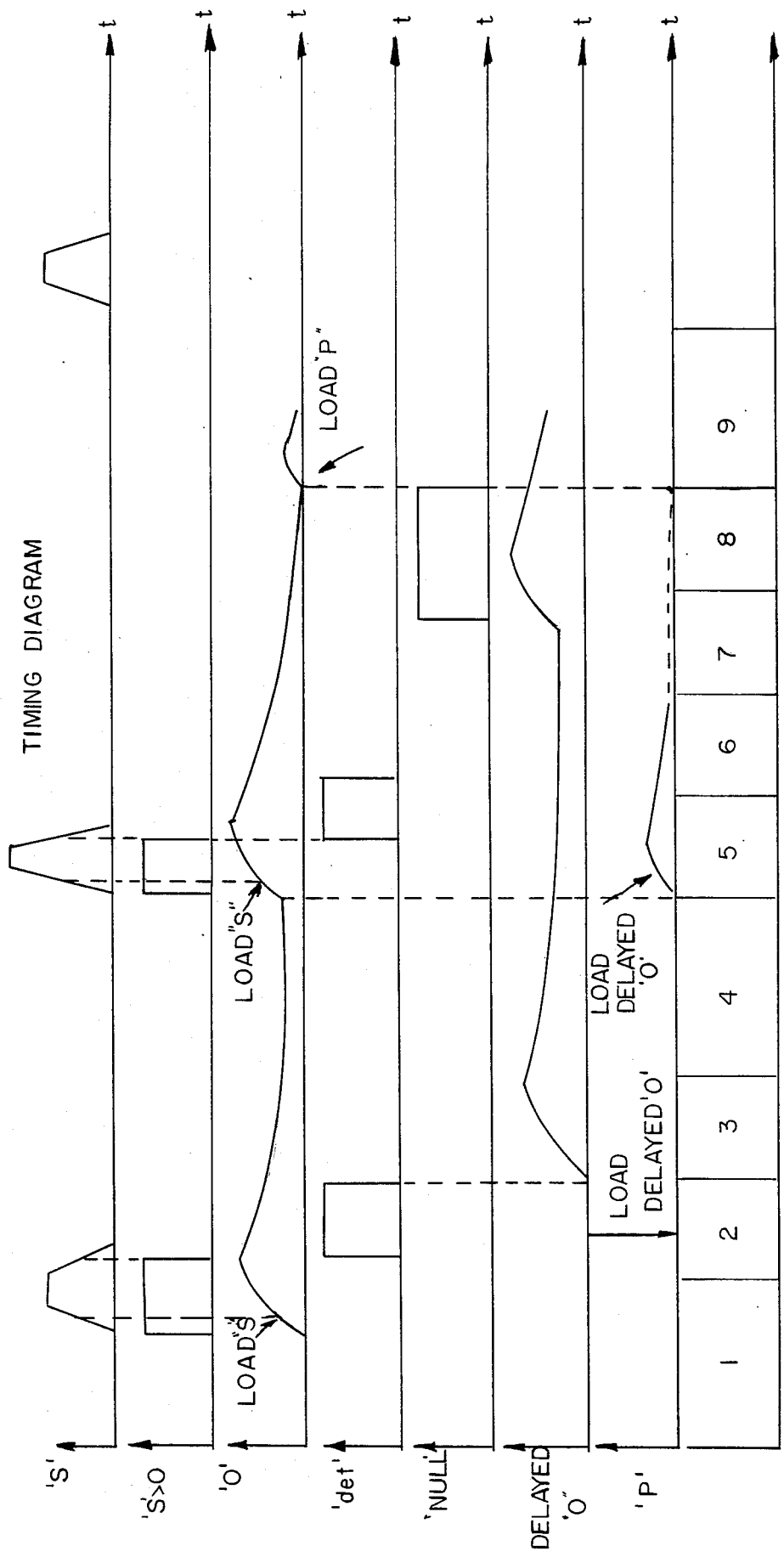

METHOD AND SYSTEM FOR DISTINGUISHING R-WAVE ELECTROCARDIOGRAPH SIGNALS FOR SYNCHRONIZING PURPOSES

FIELD OF THE INVENTION

This invention is concerned with Electrocardiogram (ECG) Systems; and more particularly, with systems using ECG signals as synchronizing or triggering sources.

BACKGROUND OF THE INVENTION

ECG signal are used not only for diagnostic purposes, such as when a trained cardiologist reads the signals but such signals also provide a timing source for synchronizing or triggering other equipment or systems to or by the heart's cycle. Such other equipment or systems may be used for example for imaging (Gamma Cameras, X-ray equipment, MR imagers etc.), diagnostic and therapeutic (e.g. heart pacers) purposes. The most commonly used method of synchronizing with the ECG signal involves feature recognition. The ECG signal comprises cyclical variations, corresponding to the electrical events occuring during variations in the heart's cycles. Certain features of ECG signals have traditionally accepted names, such as P,Q,R,S or T waves. The most prominent feature of the signals the "R" wave is the part usually used for synchromization or triggering purposes. It is generally obtained in skin surface electrodes used to detect the electrical activity of the heart. Another traditionally used variation is called "P" waves and is derived from electrodes placed in the vena cava, or in the esophagus for example.

It has long been recognized that ECG analysis provides more qualitative data when the ECG is made while the heart is under stress such as during exercise testing because most heart attacks occur when the heart is under stress. The ECG trace may give a perfectly "normal" impression when the patient is at rest, and show abnormalities only during exercise.

An ever present problem of obtaining useful signals during exercise ECG is that the movement of the patient during the exercise procedure increases the noise; and therefore, seriously deteriorates the signal-to-noise-ratio (SNR). Also the patient's movement causes muscles to generate electrical signals that compete with the heart's electrical signals. Further, the patient's stepped-up respiration causes cyclical base line wander. Additionally, the patient's perspiration acts to vary the contact resistance between the patient's skin and the sensing electrodes during the test and to thereby vary the detected signals during the test.

The noises, base line wander and varying contact resistance tend to mask the desired signals such as the "R" signal or to provide spurious signals which may be wrongfully interpreted as being a useful signal such as an "R" wave signal. The ECG signals obtained from patients with healthy hearts are harder to mask. Similarly, with a healthy heart it is harder to mistakenly interpret a noise spike as an "R" wave signal because of the regularity of ECG signals obtained from healthy hearts.

On the other hand the ECG signals from people with heart problems are irregular in time, shape and amplitude. Accordingly it is much easier to err when trying to process ECG signals obtained with an unhealthy heart especially when the signals are acquired in the noisy background inherent with exercise ECG.

The problems with noise are aggravated in many ways in systems where the ECG sitnals are analysed and processed by computers and the noise can be often easily mistaken for ECG signals.

Some of the prior art procedure and/or equipment for improving the signal-to-noise-ratio include noise filters. Whereas the noise filters are effective for line frequency caused noises, for example, they are not effective to minimize some other noises such as, for example, signals emanating from other muscles which are in the same frequency range as the heart signals. Other systems, using software, for example, to reduce base line wander take time and cannot be implemented on-line. The medical authorities (such as the A.H.A.) take a dim view of filtering out noise, for fear that a meaningful signal will also be masked out.

Timing systems based on ECG signals work in parallel to the normal recording and analysis, so that filtering is permitted on the timing portion of the ECG signal. Current systems use band pass filters to minimize low frequency base-line wander and high frequency noise. The filtered signal or its derivative is then passed through a "gate" which detects high (absolute) values. As the electrical signals differ from heart to heart, and from time to time in the same heart, and from one electrode position to another at the same time for the same heart, no universal "gate" exists. Rather, most systems use a gate that is determined by the data. The feature of the ECG signal (say, the R-wave) is considered "detected" if a value exceeding a threshold is found. This threshold is generally a certain percent (such as for example 80%) of the last determined peak. This is based on the assumption that the feature being detected is indeed the most prominent feature of the detected signal. Another safety mechanism commonly used is to blank the detector for a certain period (such as 200 msecs) after each detection, it being physiologically impossible for the heart cycle to be that short.

These types of prior art systems, like other systems, have two possible errors: false positives (a detection is declared where it should not be) and false negatives (a feature, say an R-wave, passes without detection). A system is called "sensitive" if it has few false negatives (it detects nearly all the pertinent features), and is called "specific" if it has few false positives (it detects almost only the pertinent features). For a given system, changing the system parameters usually changes both qualities, so that if the sensitivity is raised, the specificity is lowered (it detects more true features, but also more false ones). Alternatively, if the specificity is raised the system's sensitivity is lowered (it detects less errors, but also less true events.

For most purposes, with equipment or systems needing synchronization or triggering with the heart, a sensitivity of 100% is necessary (all true events are detected). Software methods are sometimes subsequently used to reduce the number of false detections, but this is time consuming.

False positives may occur either because of base-line wander, if the base-line strays by more than the said percentage, for example, of the previous peak, or because of high frequency noise or because of an external signal (say, a signal from another muscle), if its amplitude is high enough. False negative may occur either because of base-line wander, if the base-line strays in the opposite direction from the feature, say by 40% the next feature may not reach 80% of the last one. False negatives may also occur because of high frequency noise or an external signal, for example, if a false positive occurred less than the blanking period before the true feature, thereby blanking out the true feature. Noisy events such as an exercise testing are prone to both type of errors.

Accordingly, there is at present a need for systems and procedures to ensure detection of all the occurrences of certain features while reducing the number of false detections. The detection should preferably be done on-line parallel with other uses of the ECG. More particularly, there is a present need for systems and procedures to separate the noise experienced in detecting heart signals during exercise ECG tests from the useful signals.

In the following description, without meaning any loss of generality, "R wave" is referred for short, to mean in general any selected prominent feature which be used for synchronizing or triggering.

BRIEF DESCRIPTION OF THE INVENTION

According to the present invention a system is provided for use in detecting "R" waves in ECG signals acquired in noisy environments, said system comprising:

electrode means connected to a patient for detecting at least two separate ECG signals originating in the patient's heart, means for determining the slope of the detected signals, means for determining the maximal slope ( of a given sign; i.e. either positive or negative), means for comparing the time of arrival of said maximal slope to detect coincidence of signals from at least two said at least two separate ECG signals, and means for treating as "R" wave signals only those signals that have substantially the same time of arrival of said maximal slope.

A feature of the invention is the use of hardware on-line.

According to a more detailed description of the present invention a system is provided for use in detecting "R" waves in ECG signals in noisy environments, said system comprising:

electrode means connected to a patient for detecting electrical signals originated in the patient's heart;

means for finding the location of each of the ECG "R" wave in the signals (especially its time location);

means for determining whether such "R" waves coincide in the at least two separate ECG signals.

means for treating as true "R" waves only those cases where the "R" waves coincide; and means for counteracting the effects of false detections to aid in preventing false detections.

A related feature of the invention is the use of the point of maximum slope of a given sign as the definition of the "R" wave point.

A preferred version of this feature is the use of maximum negative slope. Another related feature is the use of differentiating circuits to obtain the slope of each detected signal.

Another related feature is the use of filters to remove high frequencies from the signal before differentiation, in order to minimize the effects of noise and/or respiration.

Yet another related feature of the invention is the use of circuitry to determine if there is coincidence of the maximum slopes of each of a plurality of electrodes. It has been found that the only coincident, maximal slope signals detected at different electrodes are the "R" wave signals.

The feature referred to immediately hereinabove is based on the observation that the "R" wave, which is the way the electrodes detect the passage of a strong electrical pulse along the heart's nervous system, will coincide within a very narrow time window on any electrode used (provided, of course, they are all of the same type: skin surface leads, e.g. detecting the pulse to the ventricles, or esophageal leads, detecting the pulse to the atria). Noise, on the other hand, behaves differently: baseline wander is electrode dependant, as are some types of higher frequency noises. Electronic noises will usually be of much higher frequencies and can be filtered out.

BRIEF DESCRIPTION OF THE DRAWINGS

The above mentioned and other features and objects of the invention will be better understood when considered in the light of the following description of a broad aspect of the invention taken in conjunction with the accompanying drawings, in which:

FIG. 9 is a timing diagram of the operation of the circuitry of the prior Figs.

GENERAL DESCRIPTION

Figure 1A:
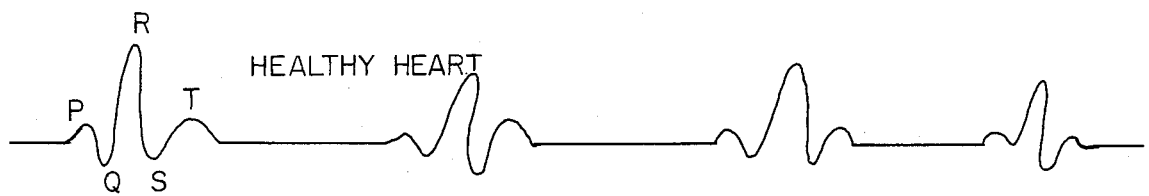
FIGS. 1 and 1*b* show ECG traces of a healthy heart and a sick heart.

The trace of FIG. 1 is a typical ECG trace of a healthy heart obtained from skin-surface sensors. The main characteristic of the healthy heart is the regularity of the signal. The larger amplitude portion of the trace is known as the "R" wave signal. The small positive signal preceeding the "R" wave is known as the "P" wave signal. The negative signal proceeding the "R" wave is the "Q" wave signal. The negative signal following the "R" wave is the "S" wave signal. The immediately following positive signal is the "T" wave signal. Note that in the healthy heart trace on a regular ECG, the waves show up with clarity and regularity.

Figure 1B:
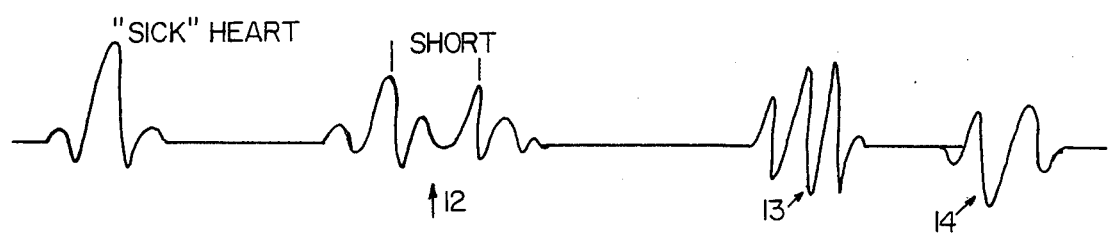

The sick heart trace of FIG. 1*b* is irregular. In addition, there are short beat sections such as at 12, repeat beat sections such as at 13 and inverted sections such as at 14.

Figure 2:
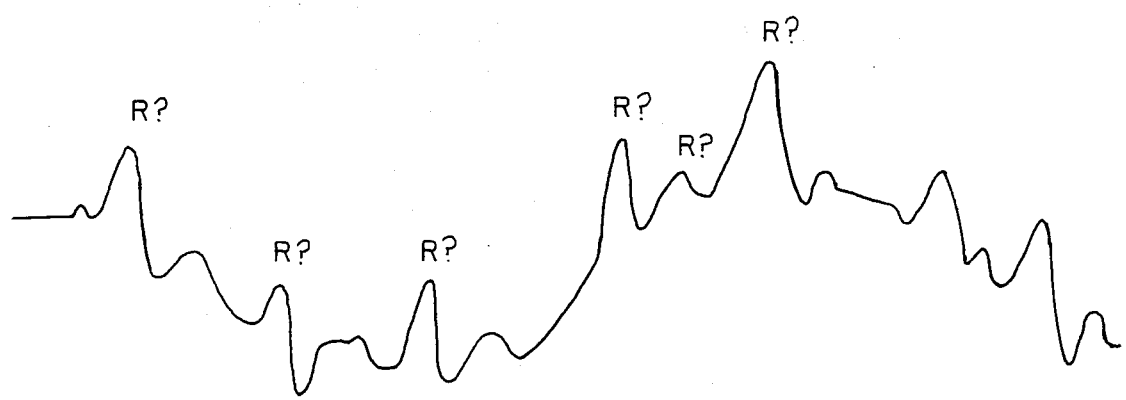
FIG. 2 shows a trace acquired during an exercise ECG test.

The trace of FIG. 2 clearly illustrates the difficulties encountered in interpreting the signals detected during an exercise ECG. From the regularity of the "R" wave signal it is a trace of a healthy heart. Note, however, the noise and the "wandering" base line. In the present day computerized signal processing equipment, the computer has to determine if indeed the large amplitude "blips" in the trace are "R" waves. The prsent invention is drawn to distinguishing the "R" waves in a reliable manner, on-line. Among the advantages of an on-line analysis is that tests can be made without having the patient spend an inordinate amount of time waiting for results and without requiring the patient to return.

In addition, several types of equipment, for example medical imaging equipment and in a particular example of Gamma Camera, use the "R" wave to synchronize their aetion with the heart cycle. For these types of equipment it is extremely important to get accurate on-line synchronizing signals such as the "R" wave detected signals. These types of equipmentneed exact times of "R" waves, and also no errors. That is they must get synchronizing signals derived from all "R" waves and from nothing by "R" waves.

Figure 3:
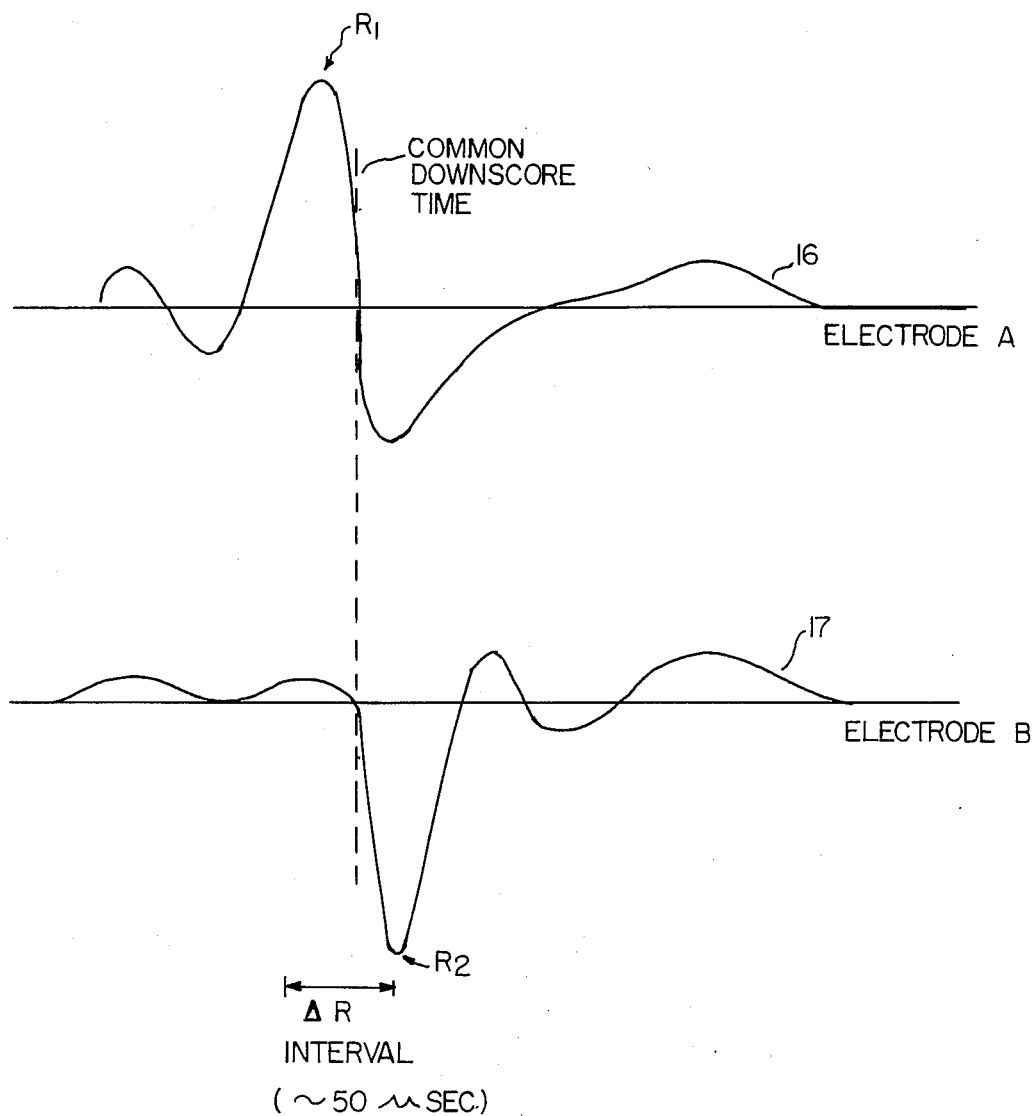
FIG. 3 shows traces from two electrodes during a test.

FIG. 3 illustrates a characteristic of the "R" wave that has been used in the past to determine the presence of "R" waves. The traces 16 and 17 in FIG. 3 are the signals detected by two different electrodes "A" and "B" referred to as a reference electrode.

Many existing "R" wave detecting circuits look for the highest absolute magnitude of the signal. This effectively accounts for the (+ or −) sign of the "R" wave which basically depends on the position of the electrode of the patient's body, but may change from patient to patient and even on the same patient from time to time. The method however is sensitive to baseline wander, to high amplitude noise, to high amplitude "T" waves, etc. Using the derivative of the signal has several advantages over using the signal itself, among which are:

The "R" wave is more prominent over other features in the derivative;

The differentiation provides low pass filtering, so that baseline wander is effectively eliminated;

The strongest down slope of the ECG signal (the largest negative peak in the derivative trace) coincides better in the different electrodes than does the absolute peak, which sometimes precedes the strongest downslopes (positive peak) and sometimes follows it (negative peaks).

The difference in time between the position R1 of the positive peak on the signal from one electrode and the position R2 of the negative peak on the signal from another electrode, both caused by the same physiological pulse, is also shown in FIG. 3.

Because of these advantages the preferred embodiment of this invention uses the slope method rather than the amplitude method. The "R" wave position is defined as the point of highest negative slope of the ECG signal.

However, the slope method has a disadvantage as derivatives are more sensitive to high frequencies, and the "R" detector may trigger more often on noise "spikes" than it would using the amplitude method. Thus, before differentiating the signal the inventive system filters out frequencies higher than some selected frequency such as 40 Hz.

This filter retains all the major features of the signal while drastically reducing the size of noise "spikes".

Figure 4:
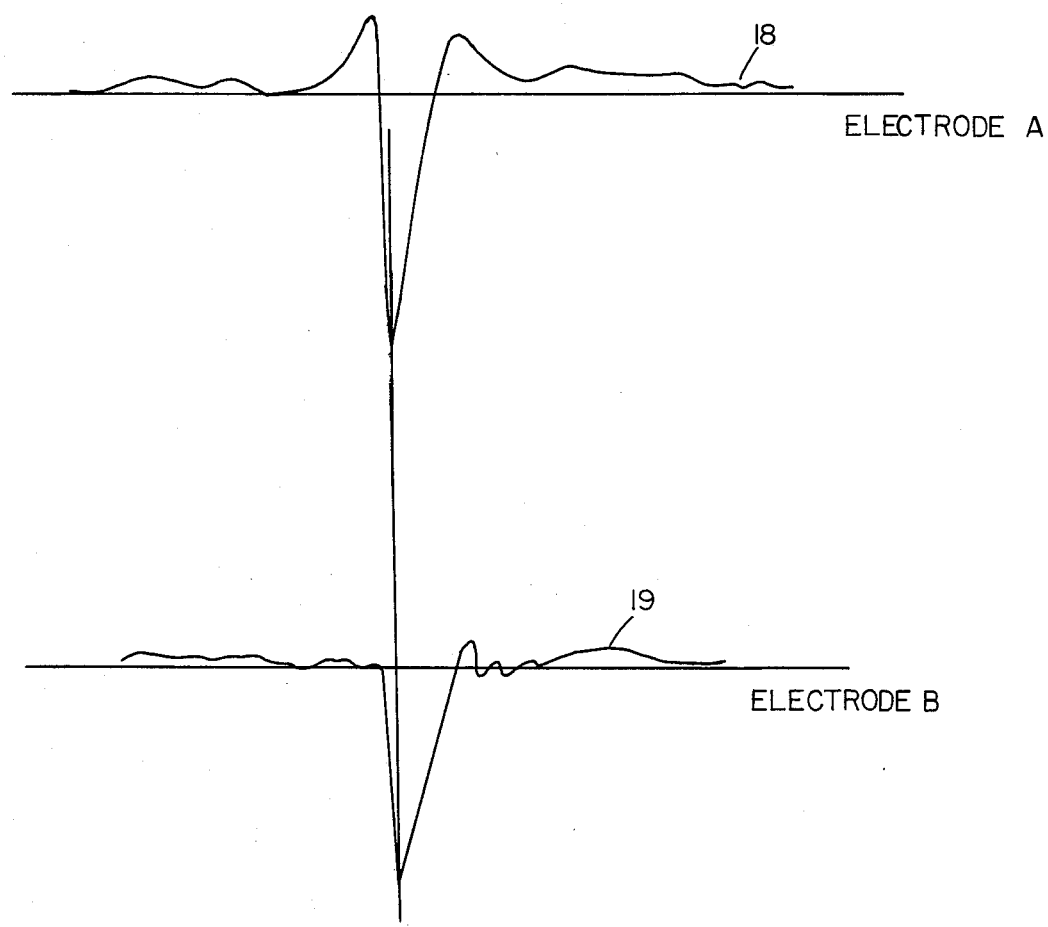
FIG. 4 is a representation of the detivatives of the signals shown FIG. 3.

FIG. 4 shows the derivatives of the signals of electrodes "A" and "B" of FIG. 3. Thus FIG. 4 illustrates that the slopes are substantially the same. The derivatives 18 and 19 of signals 16 and 17 respectively are substantially the same when the signal is an "R" wave.

FIGS. 5–8 shows in block diagram form circuitry for utilizing the down slope characteristic of the "R" waves even in the noisy backgrounds of exercise ECGs. The electrodes such as, for example, electrodes 21 and 22 schematically represent sensors and circuitry well known in the art for obtaining at least two individual ECG signals. The electrodes can be used in any configuration within the scope of the inventions such as orthogonal or non-orthogonal.

Figure 6:
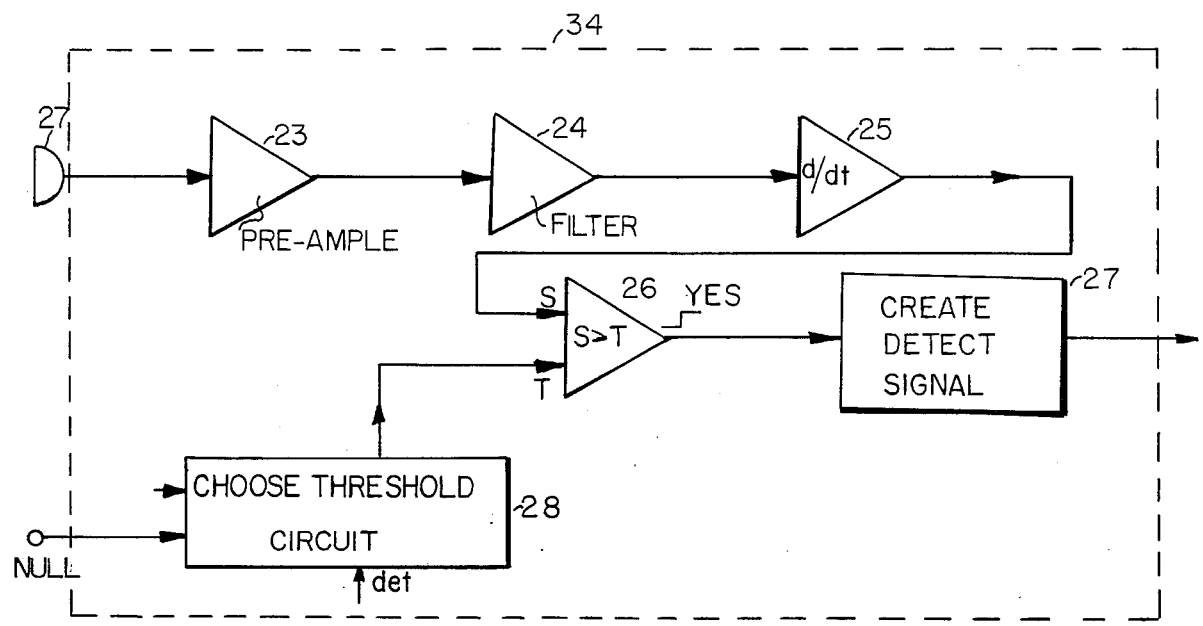
FIG. 6 is a block diagram of a single channel element of the circuit described in conjunction with FIG. 5, for detecting the "R" wave in a single channel.

As shown in FIG. 6 the at least two individual ECG signals from the electrodes are amplified and filtered by preamplifier 23 and filter 24 respectively. The filtered amplified signals are differentiated by differentiator 25 to obtain slopes. Each differentiated signal is transmitted to a first comparator 26. If the differentiated signals at the first comparator are greater than a "threshold" signal, there is a "yes" output from the comparator 26.The output signal enables a circuit 27 to generate a "det" signal. The "det" signal institutes a check of "detected R" wave coincidence with the R-waves from the other ECG signals.

Figure 5:
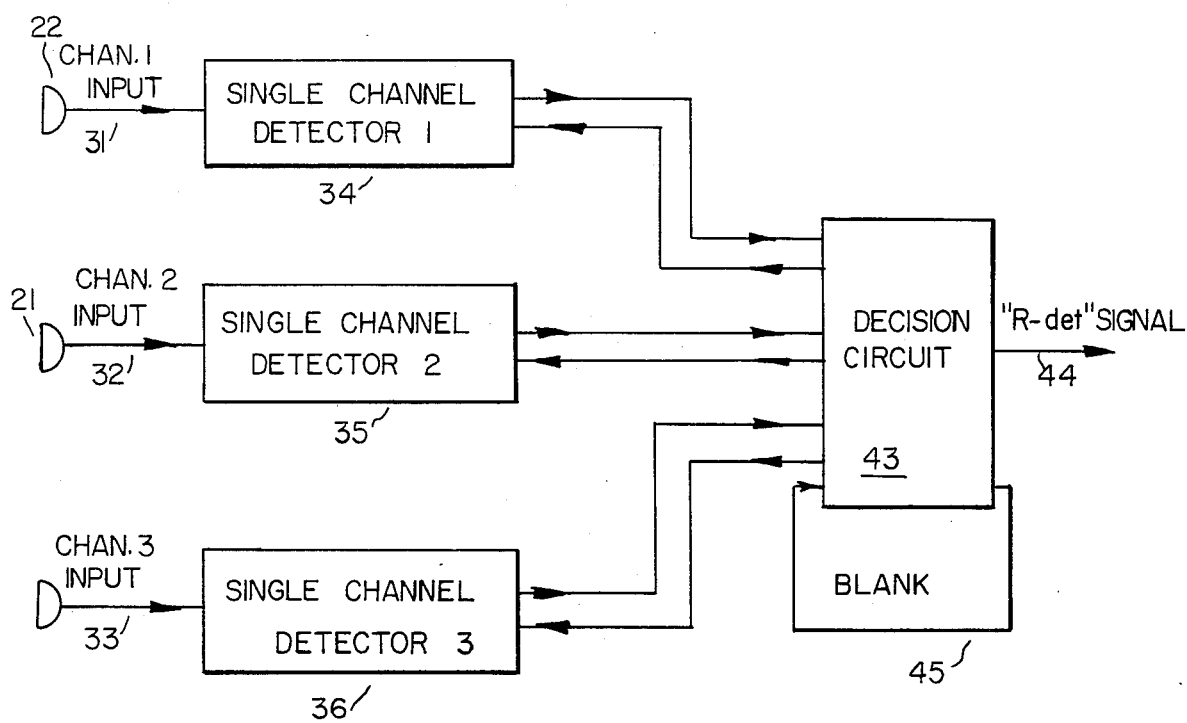
FIG. 5 is a block diagram of circuitry for distinguishing the "R" wave signal.

More particularly FIG. 5 shows in block diagram form circuitry for utilizing three ECG signals to distinguish the "R" wave even over noisy backgrounds. The signals from each of the three electrodes (not all have to be connected) enter through leads 31, 32 and 33 for three respective electrodes 21, 22 and 23. The signals then pass through single channel detectors 34,35 and 36 respectively. Each single channel detector can pass independently from a "non-detected" to a "detected" state, where it also emits a signal, shown here as "det" for short, on the output lines 37, 38 or 39 respectively.

Without limiting the generality of the invention, an example will be used to better illustrate the working of such circuitry where the "det" signal is a "high" signal lasting as long as the desired coincidence window, say 30 milliseconds for a system using derivatives of the ECG signal (a larger window, such as 80 milliseconds, is necessary for systems using the amplitude of the ECG signal).

Decision circuitry 43 then checks the three output lines 37, 38 and 39 for coincidence of the "det" signals. If the signals on all three lines coincide within the limits of the coincidence window, then an "R-detected" signal is emitted on output line 44, and a blanking signal is generated on line 45, disabling the decision circuitry from detecting another "R" wave for some physiologically determined period, say 200 milliseconds.

In the context of the example used here assume that the blank is an "active low" signal having a pulse width of 200 milliseconds. If a "det" signal occurs in one or two of the signal channel detections but not on all three, then the decision circuitry decides that no "R" wave has been detected. No "R-detected" signal and no blanking signal are emitted. Instead, the channel or channels wherein a "det" signal originated are identified, and a "null" signal is sent back on the appropriate line 40, 41 and/or 42, causing that single channel detector to modify the last threshold. Examples of circuitry for the single channel detectors and for the decision circuitry are described in the following paragraphs referring to FIGS. 6–9. It must be remembered that the circuits mentioned herein can be implemented with analog hardware, digital hardware, software or any combination thereof.

The number (3) of channels shown in FIG. 5 is an example; the inventive system comtemplates a plurality of channels, from two up. However, many existing ECG recorders/amplifiers either use three leads or use 12 leads out of which three are selected for display and output. In any case electrode 22 and pre-amplifier 23 of the single channel detector, as shown in FIG. 6, are included in the ECG recorder/amplifier and the output of pre-amplifier is shown connected to filter 24.

FIG. 6 describes in block diagram form any of the single channel detectors (34, 35 or 36 of FIG. 5). The signal from the filter 24 is differentiated with respect to time in differentiator 25, after which the time derivative signal "S" is applied to both a threshold comparator and a Choose Threshold Circuit 28. (Again, note that using the time derivative is a preferred, but not an indispensible, part of the invention). In comparator 26 the "S" signal is compared with a threshold "T". As long as the signal "S" is smaller than the threshold "T", it is discarded (for the present use; it may be used elsewhere for other purposes). When the signal "S" becomes larger then the threshold "T", the output of comparator 26 activates a pulse generator 27 which emits the "det" signal, along line 29, which may be the output line (37, 38 or 39) of any of the single channel detectors.

The pulse generator 27 is "blanked" for the duration of the "det" signal when the peak of the signal from the electrode has presumably passed. The system will thus not be triggered again until the next "R" wave or until some spurious change occurs which causes a signal "S" larger than the threshold "T".

Means are provided for modifying the threshold "T" after a false detection. As an example, the second part of the time derivative signal "S" is applied into a "choose threshold" circuit 28 which is further detailed in FIG. 7b. This circuit yields an output threshold "T" on line 21, with which the signal "S" is compared in the comparator 26. The output "T" of circuit 28 is adjusted by the "null" signal, arriving on line 40; i.e, any of the channel "null" lines 40, 41 or 42 of channels 1, 2 or 3 respectively. The null signals activate "fast decay" of the "old threshold" (as will be explained in greater detail in the explanation of FIG. 7b, i.e., circuit 28).

Figure 7A:
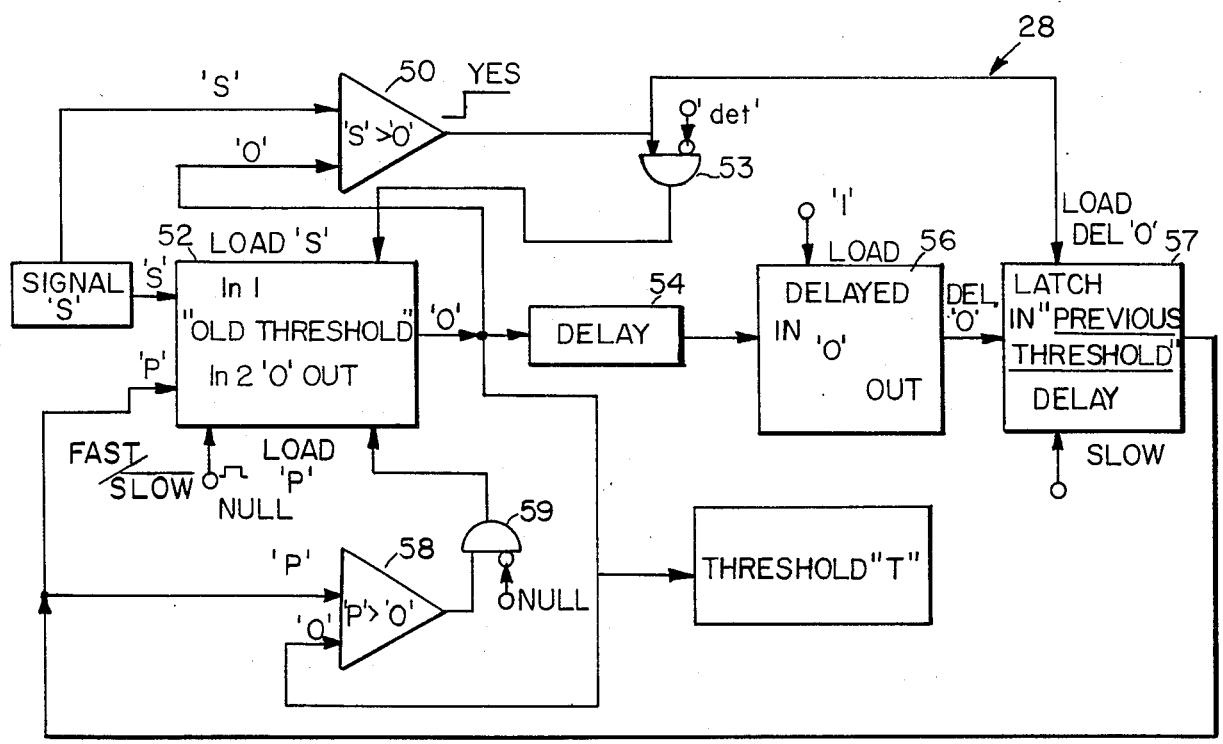
FIGS. 7*a*–7*c* are block diagrams of the threshold determining part of the single channel circuits shown in FIG. 6, including circuit blocks for setting the threshold used to determine a single channel "R" wave and for counteracting false detections to aid in preventing future false detections.
Figure 7B:
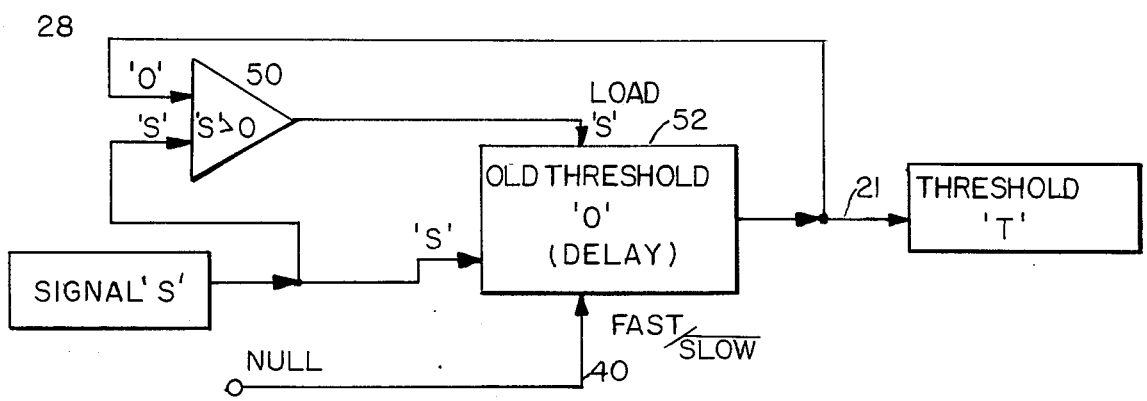
Figure 7C:
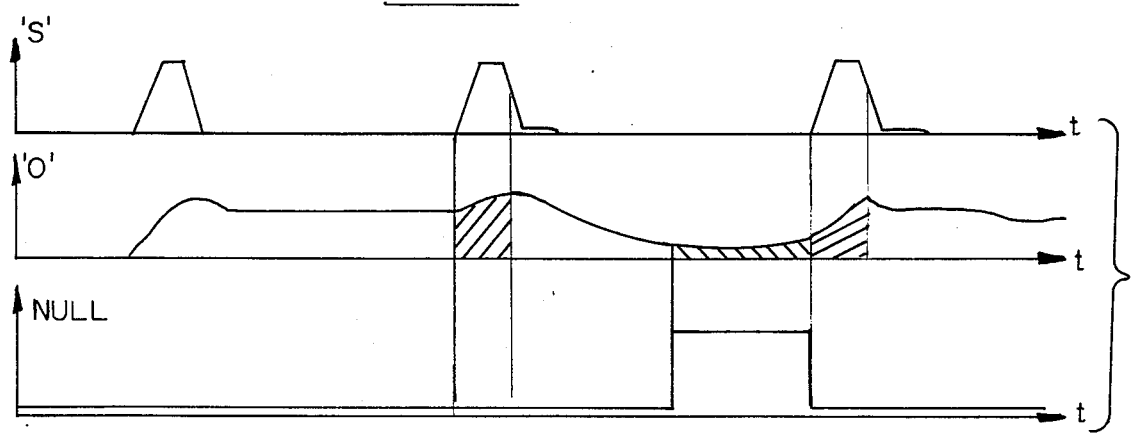

FIG. 7a and FIG. 7b show two example block diagrams of variations of circuit 28 for modifying the threshold. In general, the threshold "T" in these examples is a fraction of the last peak of the signal "S" (slope). The problem arises when the last detected peak (slope) was not an "R" wave but rather some noise generated peak. This false peak may be much larger than the normal "R" wave, especially in specific electrode positions (differing from patient to patient). This is true especially for the time differentiated signal since the sharper the spike, the greater is its enhancement by derivation.

In an example embodiment of a threshold select circuit shown in FIG. 7b, the time derivative signal "S" is compared in comparator 50 with the current or "old" threshold "O", which is stored in "old threshold" memory unit 52. If the signal "S" is less than the threshold "O" it is discarded (for this purpose; it may be used elsewhere for other purposes). If the signal "S" is larger than the threshold "O" it replaces the threshold in the memory unit 52. This causes the peak of the signal "S" to be stored in memory unit 52 immediately after it passes the circuit 50. From memory unit 52 the threshold is sent as the threshold value "T", along line 21 to the "triggering" comparator 26 (FIG. 6).

Means are provided for further modifying the threshold signal in order to deal with the normal variance in "R" wave shapes and amplitudes. For example, the value stored in memory unit 52 decays either at a "slow" rate or at a "fast" rate. The decay rate can be controlled by any means well known to those skilled in the art such as RC circuits. The decay rate is set so that the threshold decays by a fixed amount, for example 50% of its original value during an average heart beat. Thus, when the next "R" wave arrives it should be larger than the value stored in the memory unit 52 and the detector should be triggered. However, if the previous signal was a "false" detection, then the "null" signal arriving on line 40 activates a fast decay means (such as by simply switching from a large resistor to a much smaller one in an RC circuit. The "fast decay" causes the threshold stored in the memory unit 52 to decay to a small fraction of its value (say 10%) within the time duration of the "null" signal. The "choose threshold" circuit 28 is thus adjusted to provide a lower amplitude threshold at the next peak value of the signal "S" as shown in the timing diagram of FIG. 7c.

A preferred "choose threshold" circuit 28 is shown in FIG. 7a. This circuit avoids some of the noise problems encountered with the circuit of FIG. 7b. The time derivative signal "S" is directed to the comparator 50 and to memory 52. In comparator 50 the "S" signal is compared with the decayed threshold "O" which is stored in the memory unit 52. If the signal "S" is smaller than the threshold "O" it is discarded (for this purpose; it may be used elsewhere for other purposes). If the signal "S" is larger than the decayed threshold "O", then the comparator 50 provides a "yes" signal to gate circuit 53. Gate 53 has an output if there is no "det" signal. The output causes the "S" signal to be loaded into memory 52 to replace threshold "O". The output "O" of memory 52 is continuously applied to delay circuit 54. The delayed "O" is loaded into memory 56. The delayed "O" output of memory 56 is loaded into "previous threshold memory unit 57 responsive to a "yes" signal from comparator 50.

The value stored in memory unit 57 i.e. the instantaneous value "P" is applied to memory 52 and is also compared in comparator 58 with the value "O" stored in the "old threshold" memory unit 52. The output of comparator 58 provides a "yes" signal to gate 59 if "P" is greater than "O", Gate 59 provides a "load P" command in the absence of a "null" signal, as shown in the timing diagram of FIG. 9.

The choose threshold circuit provides a threshold designed to memorize false detections and none the less maintain the threshold above the level of background noise. Stage 1 of FIG. 9 is the initial stage. Subsequently a signal is detected by sensor 22. The signal is differentiated to provide the "S" signal of period 2 to 4 of FIG. 9. The "S" signal is compared to the "O" signal to provide the "yes" signal. The "yes" signal provides a load command to memory 52 until gate 53 is blanked by a "det" signal. The "O" signal decays slowly. The decaying "O" signal is delayed, stored in memory 56 and finally loaded into memory 57 responsive to the next "yes" signal from comparator 50. If a false signal was detected a "null" signal is generated which causes the "O" signal to decay at a fast rate.

Since the "P" signal is decaying at a slow rate while "O" is decaying at a fast rate eventually the "P" signal becomes greater than the "O" signal so that comparator 58 provides a "yes" signal. As soon as the "null" signal (signifying the non-coincidence) ends, comparator gate 59 provides a "load P" command to memory 52. Therefore, the new threshold is the "P" signal which is greater than the background noise.

Thus if the signal "S" results from a true "R" wave, the "O" value stored in memory 52 remains larger than the "P" value stored in memory unit 57. As they both decay at the same rate, the value "O" in memory unit 52 will remain larger than the value "P" in memory unit 57 and the value "P" is blocked by the comparator 58. However, if a "false" detection occurred, then the "null" signal causes a "fast" decay of the value stored in the memory unit 52. In that case, after the "null" signal has passed, the comparator 58 finds the "previous threshold", ("P") stored in the memory unit 57, to be larger than the value "O" stored in the memory unit 52 and the "previous threshold" value is loaded into memory 52.

Figure 8:
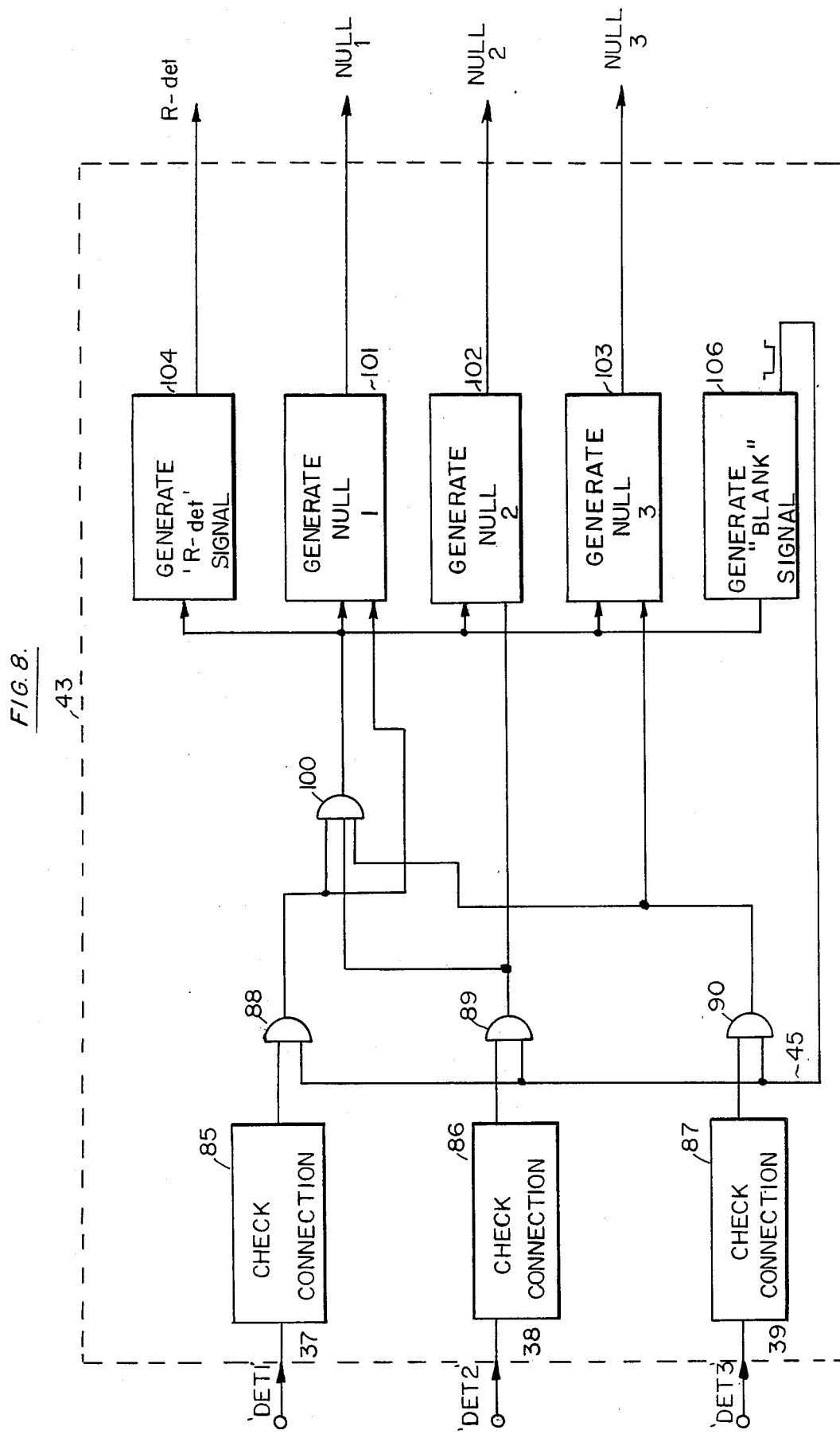
FIG. 8 is a block diagram of the decision making part of the circuit shown in FIG. 5, which is used to determine whether characteristic coincidence occurred, and if not - which electrodes have to be corrected for false detection.

FIG. 8 shows in block diagram form, details of the "decision circuit" 43 of FIG. 5. Three (in the example used here) input lines, 37, 38 and 39 lead the three "det" signals from the three single channel detectors 34, 35 and 36 respectively into the Decision circuit 43.

Each lead is checked for connection in "check connection" units 85, 86 and 87 respectively. If a lead is not connected, a "det" signal is put on that line. If the "det" signal is, for example, a "high" signal lasting 10 milliseconds, then an unconnected lead has a "high" signal thereon. Thus, when checking for coincidence, the unconnected leads will always coincide with other detections, and will not cause false rejections. A "blank" line 45, has a "det" signal for example, a "high" signal at all times except immediately after detecting an "R" wave. After detection of an "R" wave signal a "blank" signal is sent on line 45 which is opposite to a "det" signal, for example, a "low" signal lasting for 200 milliseconds. Thus, "AND" gates 88, 89 and 90 will pass the "det" signal only when the "blank" line 45 has a "det"-like signal and not during the blanking 200 miliseconds after the detection of a true "R" wave.

When the above "blank" line 45 has the active signal which enables the signals from the circuits 85, 86 and 87 to proceed, each single channel signal is connected to a three-way input "AND" gate 100, which checks for coincidence. The outputs of gates 88-90 are also each applied to "null" signal generators to cause the generation of the "null" signals 1, 2 and 3. The "null" signal generator circuits 101, 102 and 103 are disabled by the signal "A" from coincident gate 100. The output "A" is also applied to an "R" detect signal generator 104 and to the blank signal generator 106. Responsive to the "A" signal the generator 104 provides the "R-det" signal. The output of the "blank" signal generator are the previously described blanking signals.

Accordingly, the "R" wave detector operates to provide an "R det" signal indicating the detection of an "R" wave responsive to simultaneously receiving signals whose time derivative has an amplitude larger than variable respective thresholds in all the connected channels. In a particular embodiment the actual characteristic sampled and compared is the downward slope of detected "R" waves. In operation the patient is provided with a plurality of electrodes attached during an exercise program. The signals are processed through single channel detectors to determine whether or not an "R" wave has been detected. If the electrodes simultaneously receive signals that meet certain proper threshold requirements it is determined that an "R" wave has indeed been detected. Thus equipment is provided for reliably determining the detection of "R" waves during ECG exercise testings.

In operation the electrodes are analysed in multiples to distinguish with certainty the otherwise elusive "R" wave signals in real time and with reliability. The electrodes as described herein are assumed to be connected with the customary locations and polarity. A change in this polarity would of course change the signs referred to as negative to positive and vice-versa. While the invention has been described with reference to preferred embodiments, it should be understood that the described embodiments are by-way of example only and not as limitations on the scope of the invention, which is defined by the appended claims.

What is claimed is:

1. A system for distinguishing R-waves in electrocardiograph (ECG) signals, said system comprising:
   (a) a plurality of leads inputting at least two individual ECG signals from the same patient;
   (b) single channel detector means for detecting suspected R-waves in each of said at least two individual ECG signals; said single channel detector means compirsing:
      (1) means for determining the negative slopes of said ECG signals;
      (2) choose threshold means using the determined slopes for providing variable threshold signals individual to each of said at least two ECG signals;
      (3) means for comparing the determined slopes of the ECG signals to said provided threshold signals; and
      (4) means responsive to said determined slopes being more negative than said provided threshold signals for generating a "det" signal indicating a suspected R-wave;
   (c) means for determining the simultaneous receipt of said "det" signals from each of said single channel detector means; and
   (d) means operated responsive to the simultaneous receipt of the "det" signals for recognizing the suspected R-wave signals as actual R-wave signals and generating a signal indicating the detection of actual R-wave signals.

2. The system of claim 1 wherein said single channel detector means includes:
   (a) differentiating circuit means for providing the negative first derivatives of each of the at least two ECG signals to determine the negative slopes of each of said at least two ECG signals;
   (b) first comparator means in said single channel detector for comparing said first derivatives to said provided threshold signals to determine if said first derivatives are more negative than said provided threshold signals;
   (c) means responsive to said first derivative signals being more negative than said provided threshold signals for generating said "det" signals; and
   (d) means responsive to said "det" signals for storing said negative first derivative signals for use in deriving the provided threshold signals.

3. The system of claim 2 wherein said choose threshold means for providing said threshold signals comprises: means for decaying the stored negative first derivative signals, and means for modifying the provided thresholds in cases of noncoincidental receipt of said "det" signals.

4. The system of claim 3 wherein said means for modifying the provided thresholds comprises means for decaying the stored negative first derivative signals at a first rate, and means for increasing the rate of decaying to assure that large negative first derivative signals caused by false detections indicated by the non-coincidental receipt of said "det" signals are reduced to provide threshold signal values normally obtained from the first derivatives of the R-waves.

5. The system of claim 4 including previous threshold signal decaying means for providing a decayed previous threshold signal, said previous threshold signal decaying means comprising means for slowly decaying the stored and decayed negative first derivative that was the previously provided threshold signal, said means for slowly decaying being unaffected by the noncoincidental receipt of said "det" signals, means for comparing said threshold signals from said means for decaying said first derivative signals and said decayed previously provided threshold signal, and means for using, as the threshold signal, the more negative of the compared threshold signals.

6. The system of claim 5 including means for generating blanking signals responsive to the simultaneous receipt of said "det" signals, and means responsive to said blanking signals for rendering inoperative, for a fixed period of time, said means for recognizing suspected R-wave signals as actual R-wave signals.

7. The system of claim 1 wherein said single channel detector means includes filter means for filtering high frequency noise from the signals derived from said at least two individual ECG signals.

8. This system of claim 4, and means for generating null signals responsive to the non-coincidence of said "det" signals, and said means for increasing the rate of decaying being operated responsive to said null signals.

9. The system of claim 2 wherein said choose threshold means comprises:
(a) first memory means for storing the provided threshold signals as old threshold signals;
(b) means in said first memory means for decaying the stored old threshold signals at a first rate;
(c) means responsive to the non-coincidence of said "det" signals for changing said first rate to a second rate;
(d) second comparator means for comparing the old threshold signals from said first memory means to the first derivatives; and
(e) means responsive to said first derivative being more negative than said old threshold signals for loading the said first derivatives into said first memory means and to be used as the provided threshold signals in said first comparator means.

10. The system of claim 2 wherein said choose threshold means comprises:
(a) first memory means for storing the old provided threshold signals as old threshold signals;
(b) means for decaying the old threshold signals in said first memory means at a first rate of decay;
(c) second memory means for storing the old threshold signals as the previously used threshold signal after a delay period;
(d) means for decaying the delayed previously used threshold signal in said second memory at a slow rate of decay;
(e) means responsive to the non-coincidence of said "det" signals for changing said first rate of decay to a second rate which is faster than said first rate;
(f) second comparator means for comparing the currently received first derivative and the decayed old threshold signals;
(g) means for loading said first memory means with said currently received first derivatives and said second memory means with said delayed previously used threshold signal responsive to said first derivative signals being more negative than the old threshold signals;
(h) third comparator means for comparing the decayed old threshold signals and the delayed slowly decayed previously used threshold signals; and
(i) means responsive to the non-coincidence of said "det" signals and said delayed slowly decayed previously used threshold signal being more negative than said fast decayed old threshold signals for using said delayed slowly decayed previously used threshold signals as the threshold signals in said first comparator means.

11. The system of claim 1 including check connection means for checking the connection from the skin of the patient, through signal sensing electrodes, said leads, and said single channel detectors, to the said check connection means.

12. An improved method for distinguishing R-waves in electrocardiograph (ECG) signals, said method comprising the steps of:
(a) deriving at least two individual ECG signals from the same patient;
(b) determining the slopes of each of the at least two individual ECG signals;
(c) determining if the currently determined slopes are more negative than old threshold signals;
(d) using said slopes to provide new threshold signals when the slopes are more negative than said old threshold signals;
(e) generating "det" signals when said currently determined slopes are more negative than said old threshold signals;
(f) determining if the said "det" signals overlap on a time scale; and
(g) providing a signal indicating that an R-wave has been distinguished if there is an overlap.

13. The method of claim 12 including the steps of:
(a) storing said slopes for use in providing the new threshold signals; and wherein
(b) said step of providing the new threshold signals comprises correcting said old threshold signals.

14. The method of claim 13 wherein the step of correcting said old threshold signals includes decaying said stored slopes to provide decayed stored slopes as the new threshold signals.

15. The method of claim 14 wherein the step of correcting includes the steps of increasing the decay rate responsive to a non-coincidence of said "det" signals to provide a less negative stored slope as the selected threshold signal whereby large negative thresholds due to noise spikes are reduced to normal less negative values.

16. The method of claim 15 where the step of correcting includes the steps of:
(a) decaying said stored slope at a slow rate unaffected by the non-coincidence of the "det" signals;
(b) comparing the less negative stored slope to the stored slope decayed at said slow rate; and
(c) selecting the more negtive thereof as the determined threshold signals.

* * * * *